United States Patent
Morimoto et al.

(10) Patent No.: US 12,029,611 B2
(45) Date of Patent: Jul. 9, 2024

(54) ULTRASONIC ENDOSCOPE

(71) Applicant: FUJIFILM Corporation, Tokyo (JP)

(72) Inventors: Yasuhiko Morimoto, Ashigarakami-gun (JP); Toshizumi Tanaka, Ashigarakami-gun (JP); Shozo Iyama, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/053,670

(22) Filed: Nov. 8, 2022

(65) Prior Publication Data
US 2023/0107471 A1  Apr. 6, 2023

Related U.S. Application Data

(63) Continuation of application No. 16/576,476, filed on Sep. 19, 2019, now Pat. No. 11,553,894, which is a
(Continued)

(30) Foreign Application Priority Data

Mar. 31, 2017 (JP) ................................. 2017-071146

(51) Int. Cl.
  *A61B 8/00* (2006.01)
  *A61B 8/12* (2006.01)
  *A61B 8/08* (2006.01)

(52) U.S. Cl.
  CPC .............. *A61B 8/12* (2013.01); *A61B 8/4422* (2013.01); *A61B 8/445* (2013.01); *A61B 8/4494* (2013.01); *A61B 8/0841* (2013.01)

(58) Field of Classification Search
  CPC ......... A61B 8/12; A61B 8/4422; A61B 8/445; A61B 8/4494; A61B 8/0841; A61B 1/122;
(Continued)

(56) References Cited

U.S. PATENT DOCUMENTS

2005/0222493 A1  10/2005  Kohno
2007/0249940 A1  10/2007  Kohno
(Continued)

FOREIGN PATENT DOCUMENTS

CN  101384219 A  3/2009
CN  101394792 A  3/2009
(Continued)

OTHER PUBLICATIONS

Machine-generated English translation of Onishi (WO 2015/107801) (Year: 2021).*
(Continued)

*Primary Examiner* — Pascal M Bui Pho
*Assistant Examiner* — Taylor Deutsch
(74) *Attorney, Agent, or Firm* — Birch, Stewart, Kolasch & Birch, LLP

(57) ABSTRACT

An ultrasonic endoscope includes: an ultrasonic transducer having an ultrasonic vibrator; a distal end portion body disposed continuously with a proximal end side of the ultrasonic transducer; an erecting base housing portion that is disposed in the distal end portion body and has an opening which opens toward one side in a direction perpendicular to the axial direction of the distal end portion body; a treatment tool lead-out port that communicates with the inside of the erecting base housing portion; an erecting base that is disposed in the inside of the erecting base housing portion and changes a lead out direction of a treatment tool led out from the treatment tool lead-out port; and a cleaning communication hole that is formed in a wall surface on a side opposite to a side where the opening of the erecting base housing portion is disposed and communicates with an outside.

20 Claims, 12 Drawing Sheets

Related U.S. Application Data continuation of application No. PCT/JP2018/002301, filed on Jan. 25, 2018.

(58) Field of Classification Search
CPC ............ A61B 1/00098; A61B 8/4455; A61B 8/4488; A61B 1/018; A61B 1/00
See application file for complete search history.

(56) References Cited

U.S. PATENT DOCUMENTS

| | | |
|---|---|---|
| 2009/0005688 A1 | 1/2009 | Wakabayashi et al. |
| 2009/0005689 A1 | 1/2009 | Kodama et al. |
| 2013/0331696 A1 | 12/2013 | Morimoto |
| 2015/0173711 A1 | 6/2015 | Hiraoka |
| 2016/0073860 A1 | 3/2016 | Morimoto |
| 2016/0089004 A1 | 3/2016 | Morimoto |
| 2016/0206180 A1 | 7/2016 | Hosogoe |
| 2017/0014099 A1 | 1/2017 | Morimoto |
| 2018/0160889 A1 | 6/2018 | Hirano et al. |

FOREIGN PATENT DOCUMENTS

| | | | |
|---|---|---|---|
| CN | 104619266 A | 5/2015 | |
| CN | 105596028 A | 5/2016 | |
| CN | 105796042 A | 7/2016 | |
| CN | 106132312 A | 11/2016 | |
| CN | 206007283 U | 3/2017 | |
| EP | 1 992 292 A1 | 11/2008 | |
| EP | 2 671 514 A1 | 12/2013 | |
| JP | 2000185042 A * | 7/2000 | ......... A61B 1/00082 |
| JP | 2002-238906 A | 8/2002 | |
| JP | 2005-287593 A | 10/2005 | |
| JP | 2007-252458 A | 10/2007 | |
| JP | 2016-67771 A | 5/2016 | |
| JP | 2017-23480 A | 2/2017 | |
| WO | WO 2015/107801 A1 | 7/2015 | |
| WO | WO-2015107801 A1 * | 7/2015 | ............ A61B 1/123 |
| WO | WO 2017/029904 A1 | 2/2017 | |

OTHER PUBLICATIONS

Machine-generated English translation of Ouchi (JP 2000185042 A) (Year: 2023).*
European Communication pursuant to Article 94(3) EPC for corresponding European Application No. 18776305.7, dated Jan. 24, 2023.
Advisory Action issued in U.S. Appl. No. 16/576,476, dated May 17, 2022.
Chinese Office Action and Search Report, dated Aug. 6, 2021, for corresponding Chinese Application No. 201880021631.8, with an English translation of the Chinese Office Action.
English machine-generated translation of Onishi (WO 2015/107801) (2021).
European Communication pursuant to Article 94(3) EPC for corresponding European Application No. 18776305.7, dated Aug. 4, 2022.
Extended European Search Report dated Mar. 4, 2020, for corresponding European Application No. 18776305.7.
Final Office Action issued in U.S. Appl. No. 16/576,476, dated Feb. 7, 2022.
International Preliminary Report on Patentability and Written Opinion of the International Searching Authority (Forms PCT/IB/326, PCT/IB/373 and PCT/ISA/237) for International Application No. PCT/JP2018/002301, dated Oct. 10, 2019, with English translation of the Written Opinion.
International Search Report (Form PCT/ISA/210) for International Application No. PCT/JP2018/002301, dated Apr. 24, 2018, with English translation.
Japanese Notice of Reasons for Refusal dated Jun. 15, 2020, for corresponding Japanese Patent Application No. 2019-508631, with an English translation.
Non-Final Office Action issued in U.S. Appl. No. 16/576,476, dated Jul. 7, 2021.
Notice of Allowance issued in U.S. Appl. No. 16/576,476, dated Aug. 30, 2022.
Supplemental Notice of Allowance issued in U.S. Appl. No. 16/576,476, dated Sep. 14, 2022.
Chinese Office Action and Search Report for corresponding Chinese Application No. 202210309723.4, dated Nov. 3, 2023, with English translation.
Chinese Office Action and Search Report for corresponding Chinese Application No. 202210309731.9, dated Nov. 4, 2023, with English translation.

* cited by examiner

ULTRASONIC ENDOSCOPE

CROSS-REFERENCE TO RELATED APPLICATIONS

This application is a Continuation of U.S. patent application Ser. No. 16/576,476, filed on Sep. 19, 2019, which is a Continuation of PCT International Application No. PCT/JP2018/002301 filed on Jan. 25, 2018, which claims priority under 35 U.S.C. § 119(a) to Japanese Patent Application No. 2017-071146 filed on Mar. 31, 2017. Each of the above applications are hereby expressly incorporated by reference, in their entirety, into the present application.

BACKGROUND OF THE INVENTION

1. Field of the Invention

The present invention relates to an ultrasonic endoscope, and, in particular to an ultrasonic endoscope including an erecting base for erecting a treatment tool that is led out from an opening formed in a distal end body of an endoscope insertion section.

2. Description of the Related Art

Some existing ultrasonic endoscopes known to date include an erecting base and an erecting base housing for containing the erecting base in a distal end body of an insertion section that is inserted into a body cavity. Such an ultrasonic endoscope can erect a treatment tool, which is inserted into a treatment tool insertion channel and led out from a treatment tool lead-out portion at the distal end body, and can also adjust the lead-out direction of the treatment tool by changing the erection angle of the erecting base.

For example, JP2005-287593A describes an endoscope configured as follows: a treatment tool lead-out portion has an erecting base, an erecting lever is coupled to the erecting base via a rotation shaft, an operation wire is coupled to the erecting lever, and the operation wire can be pushed or pulled by operating an operation unit that is disposed continuously with a proximal end portion of an insertion section.

SUMMARY OF THE INVENTION

It is necessary to clean an endoscope every time the endoscope is inserted into a body cavity of a subject. A duodenoscope including an erecting base has a removable distal end cap, so that the erecting base and the surrounding part can be easily cleaned by removing the distal end cap. However, a distal end cap of an ultrasonic endoscope is irremovable, because the ultrasonic endoscope has an ultrasonic vibrator on the distal end side and the ultrasonic vibrator needs to be liquid-tight. Therefore, cleaning of the erecting base and the surrounding part can be performed only by inserting a cleaning tool, such as a brush or a syringe, through an opening in an erecting base housing portion. Thus, improvement in ease of cleaning the back surface and the like of the erecting base has been demanded.

The present invention has been made under such circumstances, and an object of the present invention is to provide an ultrasonic endoscope that can improve the ease of cleaning the ultrasonic endoscope, in particular, the ease of cleaning an erecting base and the surrounding part.

To achieve the object, the present invention provides an ultrasonic endoscope including: an ultrasonic transducer that has an ultrasonic vibrator; a distal end portion body that is disposed continuously with a proximal end side of the ultrasonic transducer; an erecting base housing portion that is disposed in the distal end portion body and that has an opening whose opening direction is one side in a first direction that is perpendicular to an axial direction of the distal end portion body or whose opening direction is a direction that has a component toward one side in the first direction and a component toward a distal end side in the axial direction of the distal end portion body; a treatment tool lead-out port that communicates with an inside of the erecting base housing portion and from which a treatment tool is led out; an erecting base that is disposed in the inside of the erecting base housing portion and that changes a lead out direction of the treatment tool led out from the treatment tool lead-out port; and a cleaning communication hole that is formed in a wall surface on a side opposite to a side where the opening of the erecting base housing portion is disposed and that communicates with an outside.

With the present invention, by disposing the cleaning communication hole on a side opposite to a side on which the opening of the erecting base housing portion is disposed, it is possible to insert a cleaning tool, such as a brush or a syringe, from the cleaning communication hole, and cleaning of the back side of the erecting base and a part surrounding the back side can be performed. Thus, the ease of cleaning the erecting base and the surrounding part can be improved.

According to another aspect of the present invention, preferably, the ultrasonic endoscope includes an observation window that is disposed in the distal end portion body and through which a subject is observed, and a position of the observation window in the axial direction of the distal end portion body is located on a proximal end side relative to the erecting base housing portion.

With this aspect, by locating the position of the observation window on the proximal end side relative to the erecting base housing portion, the opening of the erecting base housing portion can be placed within the field of view of the observation window. Accordingly, a treatment tool can be checked through the observation window from a position where the treatment tool is led out from the opening, and treatment can be reliably performed at a target position.

According to another aspect of the present invention, preferably, a position of the observation window in the first direction is located on a side opposite to the cleaning communication hole when a position of the opening is defined as a reference position.

This aspect defines the positions of the observation window and the opening in the first direction. The observation window is disposed above the opening when "above" is defined, with respect to the opening opposite, as a side opposite to the cleaning communication hole, that is, a side toward which the opening is open from the erecting base housing portion. Accordingly, a blind area where a treatment tool led out from the opening is not placed in the field of view can be reduced, and therefore treatment can be reliably performed while checking through the observation window.

According to another aspect of the present invention, preferably, the observation window is disposed offset from the erecting base housing portion in a second direction that is perpendicular to the first direction.

With this aspect, because the observation window is disposed offset from the erecting base housing portion in the second direction, when the erecting base is erected, blocking of the field of view of the observation window by a treatment tool and the erecting base can be prevented.

According to another aspect of the present invention, preferably, the ultrasonic endoscope has a signal cable that is connected to the ultrasonic vibrator; and, when the signal cable and the erecting base housing portion are projected onto a plane that is perpendicular to the first direction, the signal cable is disposed in a region that is different from a region where the erecting base housing portion is disposed.

With this aspect, because the position of the erecting base housing portion and the position of the signal cable are different positions in a plane perpendicular to the first direction, that is, in plan view, the erecting base housing portion can be moved closer to the opening of the cleaning communication hole in the distal end portion body. Accordingly, the length of the cleaning communication hole can be reduced, and cleaning of the erecting base can be easily performed.

According to another aspect of the present invention, preferably, when viewed in the axial direction of the distal end portion body, the erecting base housing portion is disposed offset from a center position of the distal end portion body in a second direction that is perpendicular to the first direction, and the signal cable is disposed in the second direction of the erecting base housing portion.

This aspect defines the positional relationship between the erecting base housing portion and the signal cable. The erecting base housing portion can be disposed offset from the center position of the distal end portion body in the second direction, and the signal cable can be disposed on the opposite side in the second direction. By disposing in this way, the length of the cleaning communication hole can be reduced, and the observation window can be easily disposed offset from the erecting base housing portion in the second direction.

According to another aspect of the present invention, preferably, when viewed in the axial direction of the distal end portion body, among a plurality of the signal cables that are connected to the ultrasonic vibrator, at least one of the signal cables is disposed on one side in a second direction of the erecting base housing portion, and at least another of the signal cables is disposed on the other side in the second direction of the erecting base housing portion.

This aspect defines the positional relationship between the erecting base housing portion and the signal cables. By disposing the plurality of signal cables, which are connected to the ultrasonic vibrator, on both sides of the erecting base housing portion in the second direction when viewed in the direction of the axis of the distal end portion body, the erecting base housing portion can be moved closer to the opening of the cleaning communication hole, and the length of the cleaning communication hole can be reduced.

According to another aspect of the present invention, preferably, the distal end portion body comprises a cover that is removably attached to the cleaning communication hole.

With this aspect, when inserting the distal end portion body into a body cavity, by attaching the cover to the cleaning communication hole, contamination of the erecting base housing portion and the erecting base can be suppressed. Moreover, when cleaning the distal end portion body, by removing the cover from the cleaning communication hole, cleaning can be performed by inserting a cleaning tool from the cleaning communication hole.

According to another aspect of the present invention, preferably, an expression $H1 \leq H2$ holds, where, in the first direction of the distal end portion body, H1 is a shortest distance from the cleaning communication hole to the opening, and H2 is a longest distance from the cleaning communication hole to an outer peripheral surface of the ultrasonic transducer.

With this aspect, due to the disposition such that the above expression holds, where, in the first direction, H1 is a shortest distance from the cleaning communication hole to the opening, and H2 is a longest distance from the cleaning communication hole to an outer peripheral surface of the ultrasonic transducer, a treatment tool led out from the opening can be made closer to the ultrasonic transducer. By making the treatment tool be closer to the ultrasonic transducer, displacement of an insertion position due to horizontal displacement or the like of a treatment tool led out from the opening can be suppressed, and treatment can be performed at a target position.

According to another aspect of the present invention, preferably, the ultrasonic transducer has an ultrasound transmitting/receiving surface that is formed in a curved shape in the axial direction of the distal end portion body.

The present invention can be preferably used for a convex-type ultrasonic endoscope in which the ultrasound transmitting/receiving surface of the ultrasonic transducer has a curved shape in the axial direction of a distal end portion body.

With the ultrasonic endoscope according to the present invention, by disposing a cleaning communication hole in a wall surface of the erecting base housing portion on a side opposite to a side where the opening is disposed, cleaning of the back side of the erecting base can be performed by inserting a cleaning tool from the cleaning communication hole. Accordingly, cleaning of the back side of the erection base, which has been difficult to perform from the opening, can be easily performed, and the ease of cleaning the erecting base and the surrounding part can be improved.

DESCRIPTION OF THE PREFERRED EMBODIMENTS

Hereafter, an ultrasonic endoscope according to the present invention will be described with reference to the drawings.

Ultrasonic Endoscope

Figure 1:
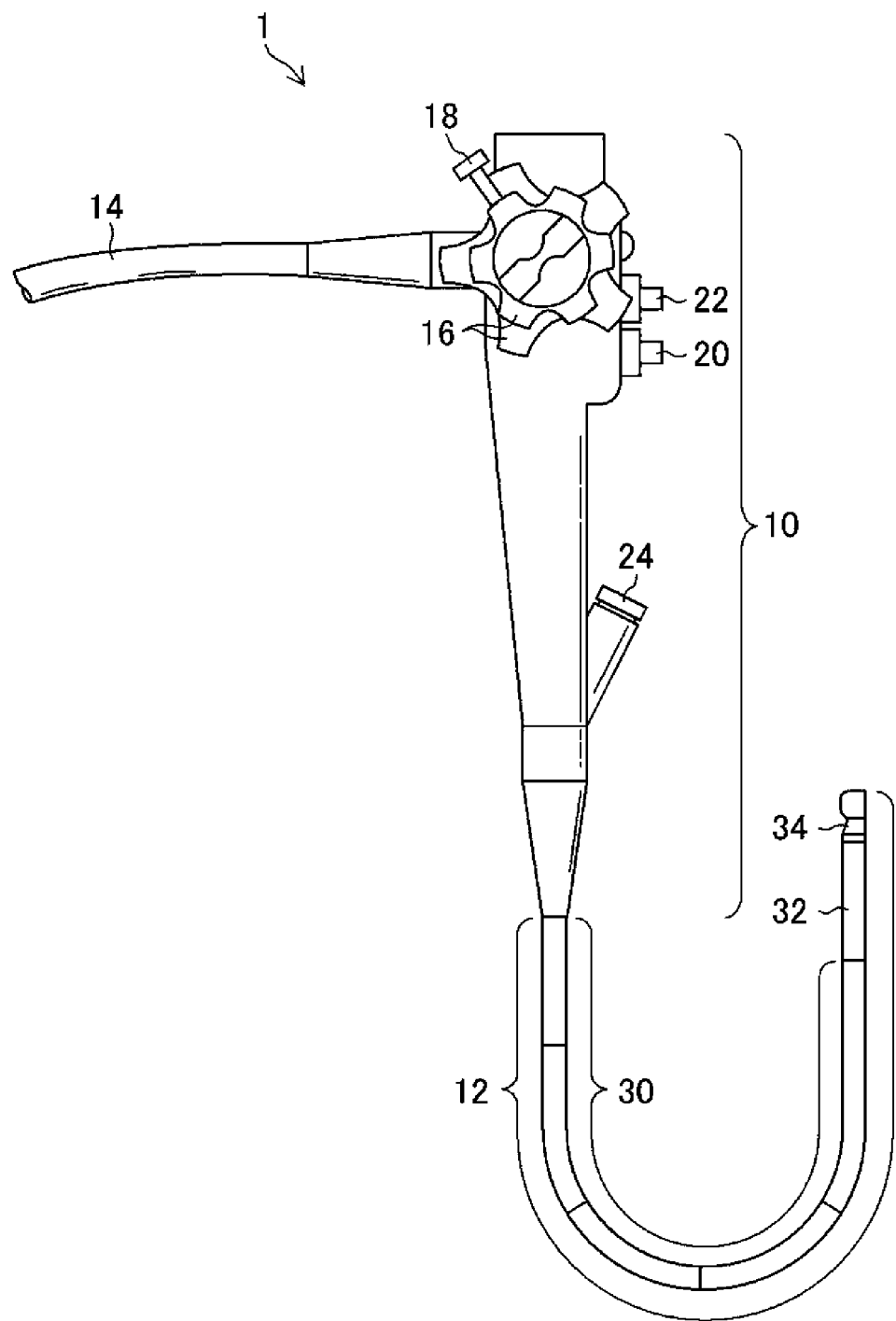
FIG. 1 is an overall view of an ultrasonic endoscope according to the present invention.

FIG. 1 is an overall view of an ultrasonic endoscope 1 to which the present invention is applied.

The ultrasonic endoscope 1 (hereafter, simply referred to as "the endoscope 1") illustrated in the figure includes an operation unit 10 that an operator grips to perform various operations, an insertion section 12 that is inserted into a body cavity of a patient, and a universal cord 14. The endoscope 1 is connected, via the universal cord 14, to system component devices (not shown) of an endoscope system, such as a processor device and a light source device.

The operation unit 10 has various operation members that are operated by an operator, such as an angle knob 16 whose functions will be described below as necessary, an erecting operation lever 18, an air/water supply button 20, and a suction button 22.

The operation unit 10 has a treatment tool insertion opening 24 from which a treatment tool is inserted into a treatment tool insertion channel, which extends through the insertion section 12.

The insertion section 12 extends from a distal end of the operation unit 10, and has a small-diameter elongated shape as a whole.

The insertion section 12 is composed of a soft portion 30, a bending portion 32, and a distal end portion 34, in order from the proximal end side toward the distal end side.

The soft portion 30 occupies most part of the insertion section 12 from the proximal end side, and has flexibility with which the soft portion 30 can be bent in any directions. When the insertion section 12 is inserted into the body cavity, the soft portion 30 is bent along an insertion path into the body cavity.

The bending portion 32 can be bent in the up-down direction and the left-right direction by rotating the angle knob 16 of the operation unit 10. By bending the bending portion 32, the distal end portion 34 can be directed in a desired direction.

As described below in detail with reference to FIGS. 2 to 4, the distal end portion 34 includes an ultrasonic transducer 50 that has one or more ultrasonic vibrators, and a distal end portion body 36 that is disposed continuously with the proximal end side of the ultrasonic transducer 50. The distal end portion body 36 has an erecting base housing portion 62, and the erecting base housing portion 62 has an opening 58 that opens in a first direction that is perpendicular to the direction of an axis 38 of the distal end portion body 36. Moreover, the distal end portion body 36 has a treatment tool lead-out port 80 that communicates with the inside of the erecting base housing portion 62 and from which a treatment tool is led out. Furthermore, in the erecting base housing portion 62, an erecting base 60, which changes the lead-out direction of a treatment tool led out from the treatment tool lead-out port 80, is disposed. The axis 38 of the distal end portion body 36 is a line that coincides with or is parallel to the longitudinal axis of the insertion section 12 of FIG. 1.

The universal cord 14 illustrated in FIG. 1 contains an electric cable, a light guide, and a fluid tube. The universal cord 14 includes a connector at an end portion thereof (not shown). By connecting the connector to predetermined system component devices of the endoscope system, such as a processor device and a light-source device, electric power, control signals, illumination light, liquid, gas, and the like that are necessary to operate the endoscope 1 are supplied from the system component devices to the endoscope; and data of an observation image obtained by the image-capturing portion and data of an ultrasound image obtained by the ultrasonic transducer are transmitted from the endoscope 1 to the system component devices. The observation image and the ultrasound image transmitted to the system component devices are displayed on a monitor, and an operator and the like can observe the images.

Structure of Distal End Portion

First Embodiment

Next, the structure of the distal end portion 34 of the insertion section 12 will be described. FIG. 2 is an external perspective view of the distal end portion 34 according to a first embodiment. FIG. 3 is a plan view (top view). FIG. 4 is a side sectional view. FIG. 5 is a bottom view.

The distal end portion 34 has the distal end portion body 36 that forms the outer wall and the inner partition wall thereof. Components disposed in the distal end portion body 36 are disposed and held in housing portions (housing chambers) that are included in the distal end portion body 36.

Although details are omitted, a part of the distal end portion body 36 is removable as a separated block. The components can be installed in a predetermined housing portion in a state in which the separated block is removed. After installing the components in the housing portions, by attaching the separate block to the distal end portion body 36, the components can be disposed and held in the housing portions and fixed to the distal end portion 34.

The distal end portion body 36 is made of an insulating material having insulating properties, which is, for example, a resin material that is a plastic or the like, such as a methacrylate resin or polycarbonate.

As illustrated in FIGS. 2 to 5, the distal end portion 34 is composed of a base member 40 that is included in the distal end portion body 36, and an extension portion 42 that extends from the base member 40 toward the distal end side and holds the ultrasonic transducer 50.

That is, in the extension portion 42, the ultrasonic transducer 50 of a convex-type is disposed. The ultrasonic transducer 50 has an ultrasound transmitting/receiving surface 52 that is formed by arranging ultrasonic vibrators, for transmitting and receiving ultrasound, in a curved shape in the direction of the axis 38 of the distal end portion body 36. The ultrasonic transducer 50 obtains data for generating an ultrasound image of a body tissue. The number of ultrasonic vibrators is not limited and may be one; or two or more ultrasonic vibrators may be disposed.

Figure 2:
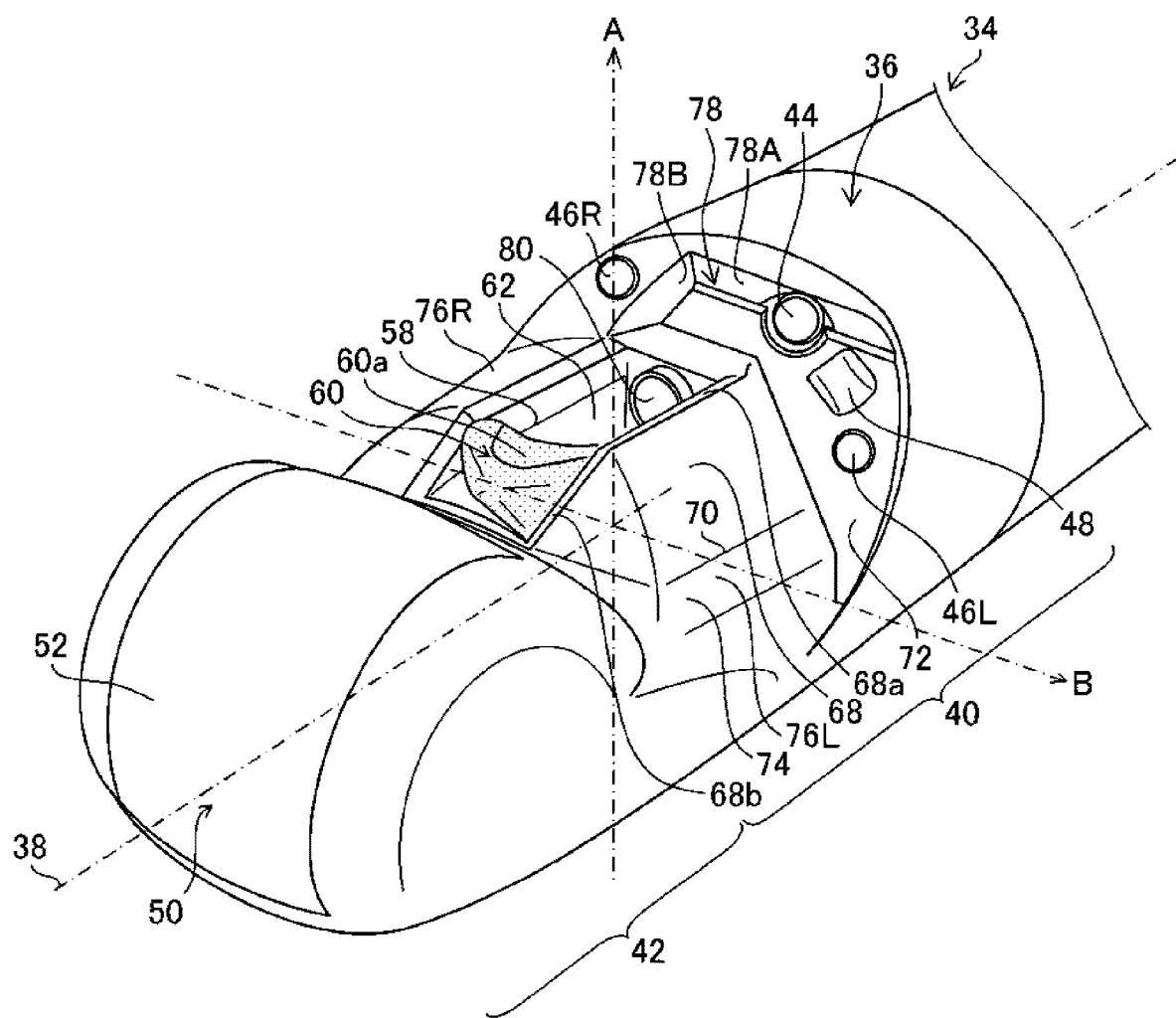
FIG. 2 is an external perspective view of a distal end portion of an insertion section according to a first embodiment.
Figure 3:
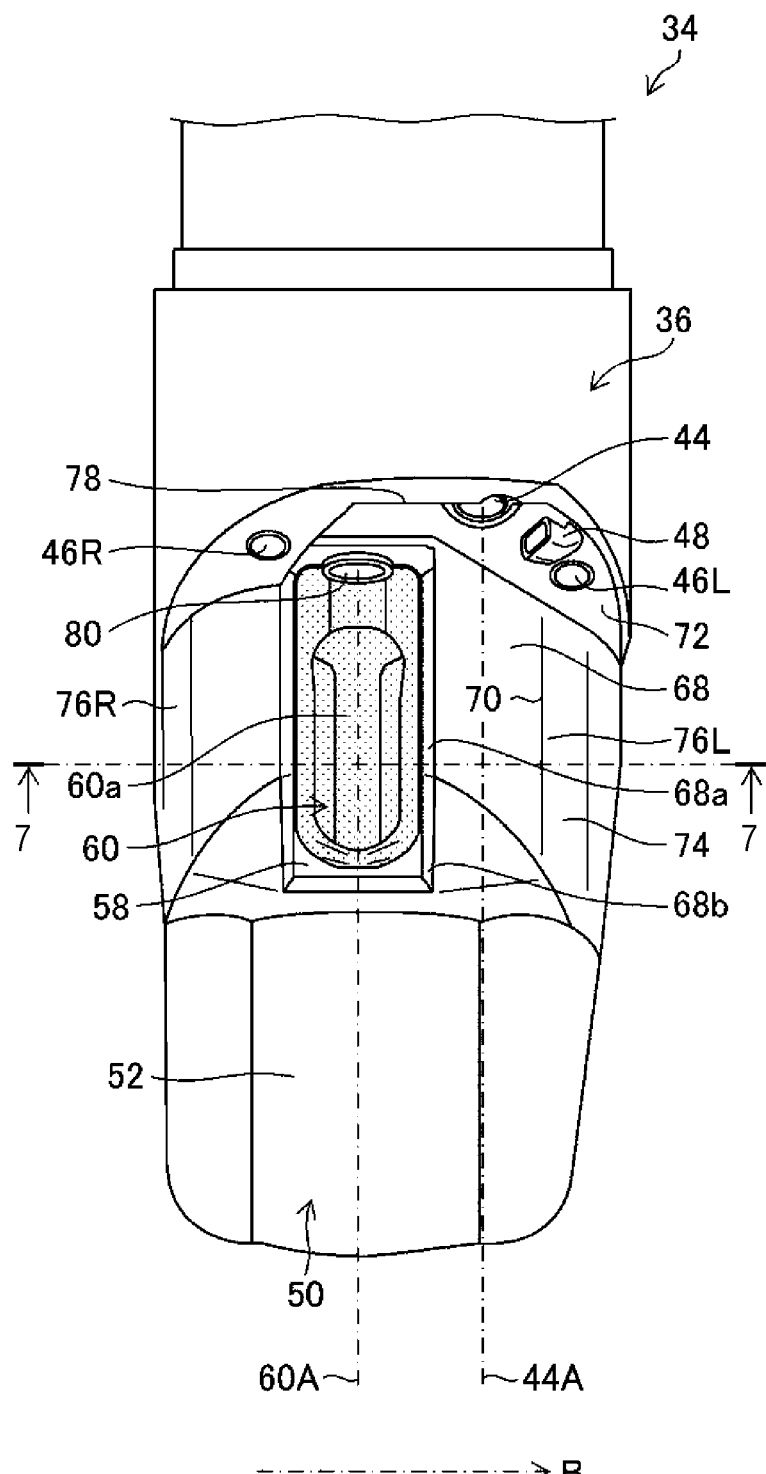
FIG. 3 is an external plan view (top view) of the distal end portion of the insertion section according to the first embodiment.

As illustrated in FIGS. 2 and 3, the distal end portion body 36 has an observation window 44, illumination windows 46L and 46R, an air/water supply nozzle 48, the opening 58 for leading out a treatment tool, and a standing wall portion 68 disposed around the opening 58.

The opening 58 is formed at the center of an opening forming surface 70 that is located on the extension portion 42 side of the distal end portion body 36. From the opening 58, a treatment tool is led out to an ultrasound scanning range of the ultrasonic transducer 50. The opening 58 is formed in the opening forming surface 70 so that an opening direction thereof is toward one side, in a first direction that is perpendicular to the direction of the axis 38 of the distal end portion body 36, of the erecting base housing portion 62 of the distal end portion body 36. The opening 58 may be formed so that an opening direction thereof has a component toward the one side in the first direction and a component toward the distal end side in the direction of the axis 38 of the distal end portion body 36. That is, the opening may be formed so as to be open upward (toward the one side in the first direction) toward the distal end of the distal end portion body 36. Here, the term "opening direction" refers to a direction normal to a surface surrounded by the edge of the opening 58. In the present description, the term "the first direction" refers to a direction, as indicated by arrow A in FIG. 4, that is perpendicular to the axis 38 of the distal end portion body 36 and in which the opening 58 of the erecting base housing portion 62 is formed. The term "second direction" refers to a direction, as indicated by arrow B in FIG. 2, that is perpendicular to the axis 38 of the distal end portion body 36 and to the first direction indicated by arrow A. The phrase "one side in the first direction" refers to a side toward which the opening 58 opens. In the present description, the one side in the first direction may be referred to as "up" and "upward", and the other side in the first direction may be referred to as "down" and "downward".

A treatment tool is inserted from the treatment tool insertion opening 24 of the operation unit 10 shown in FIG. 1 toward the insertion section 12. The opening forming surface 70, which is illustrated in FIG. 3, may be parallel to the axis 38 of the distal end portion body 36, or may be inclined downward toward the distal end side of the distal end portion 34. The opening 58 is a portion through the treatment tool is led out from the erecting base housing portion 62 via the erecting base 60 (described below).

Figure 4:
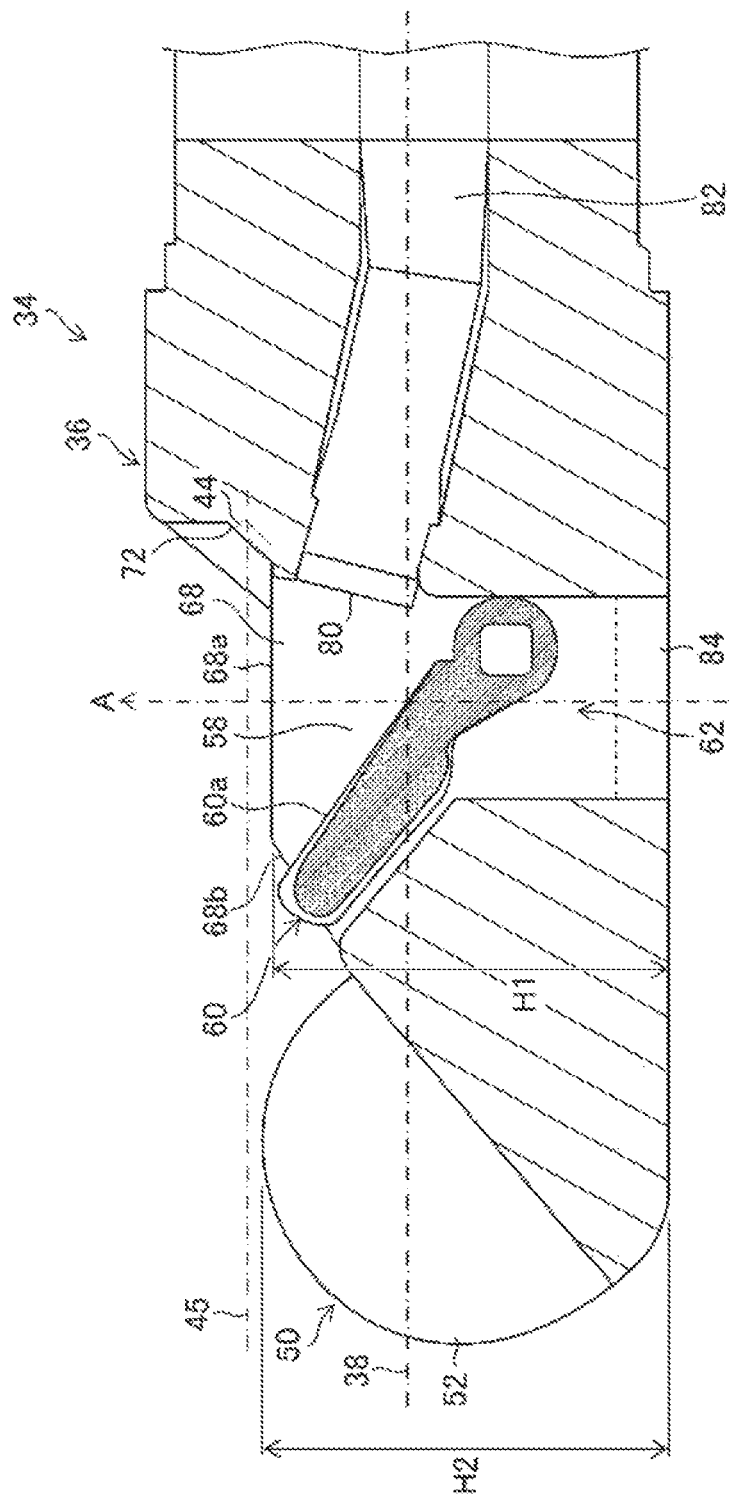
FIG. 4 is a side sectional view of the distal end portion of the insertion section according to the first embodiment.
Figure 5:
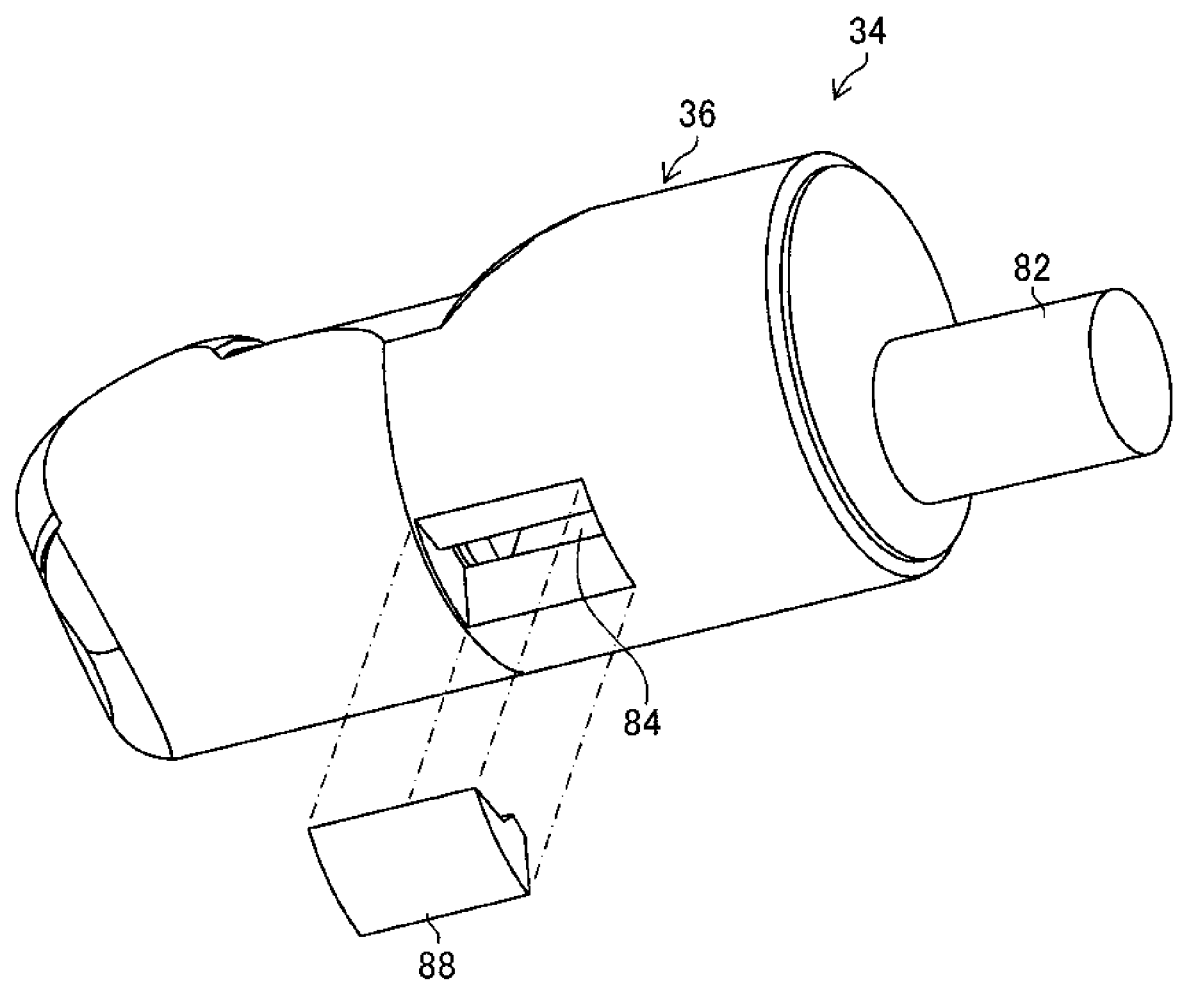
FIG. 5 is a bottom view of the distal end portion of the insertion section according to the first embodiment.

As illustrated in FIG. 4, the treatment tool lead-out port 80 is disposed on the proximal end side of the erecting base housing portion 62. The treatment tool lead-out port 80 communicates with the treatment tool insertion opening 24 of the operation unit 10 (see FIG. 1) via a treatment tool insertion channel 82 extending through the insertion section 12. A treatment tool inserted from the treatment tool insertion opening 24 is led out from the treatment tool lead-out port 80 (see FIG. 4) to the erecting base housing portion 62.

The erecting base 60 is disposed at a position in the erecting base housing portion 62 in front of the treatment tool lead-out port 80. The erecting base 60 is made of a metal material, such as stainless steel, and has, on an upper side thereof, a guide surface 60a that is a concave surface that is curved upward from the proximal end side to the distal end side of the distal end portion body 36. A treatment tool led out from the treatment tool lead-out port 80 becomes curved upward along the guide surface 60a with respect to the direction of the axis 38 of the distal end portion body 36 (for example, the longitudinal direction of the insertion section 12) and is led out to the outside from the opening 58 on the upper side of the erecting base housing portion 62 and the edge of the standing wall portion 68.

The erecting base 60 can be erected by operating the erecting operation lever 18 illustrated in FIG. 1. The lead-out direction (lead-out angle) of a treatment tool led out from the opening 58 can be adjusted by erecting the erecting base 60 and by adjusting the erection angle from the prostrate state.

Figure 6:
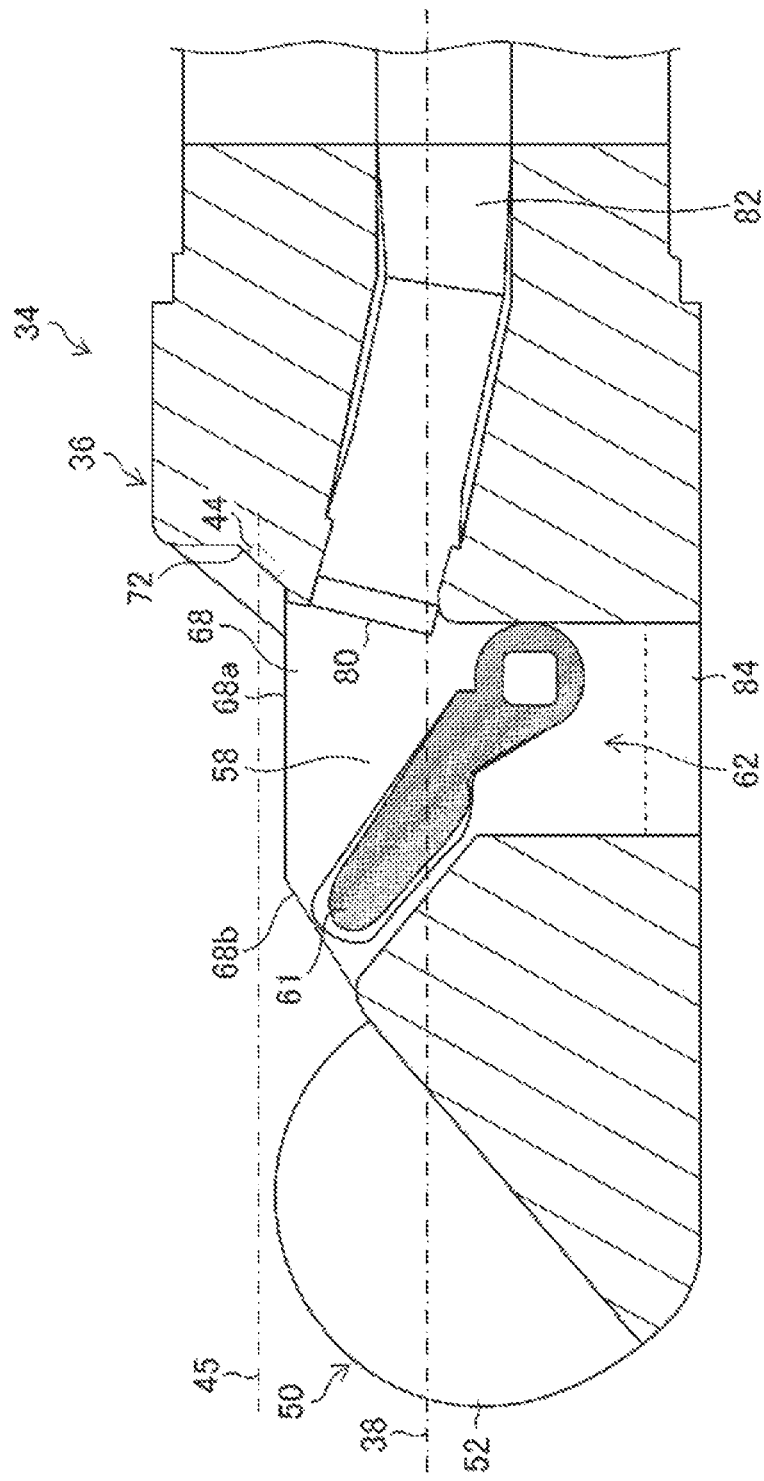
FIG. 6 is a side sectional view of an erecting base of a distal end portion according to a modification.

FIG. 6 is a side sectional view of an erecting base 61 according to a modification. Here, with the erecting base 60 according to the first embodiment, which is illustrated in FIG. 4, when the erecting base 60 is in a prostrate position (a fully lowered state), a distal end part of the erecting base 60 protrudes from a front edge 68b of the standing wall portion 68. In contrast, when the erecting base 61 illustrated in FIG. 6 is in a fully lowered state, the distal end part of the erecting base 61 does not protrude from the standing wall portion 68, and the entirety of the erecting base 61 is disposed in the erecting base housing portion 62. With a structure such that the erecting base 61 is disposed in the erecting base housing portion 62 in the fully lowered state as in the erecting base 61 illustrated in FIG. 6, the insertion section 12 can be smoothly inserted into a human body.

The treatment tool insertion channel 82 illustrated in FIGS. 4 and 6 is coupled also to a suction channel (not shown). By operating the suction button 22 illustrated in FIG. 1, a bodily fluid or the like can be sucked through the opening 58.

As illustrated in FIG. 4, by locating the position of the opening 58 on the proximal end side of the ultrasonic transducer 50 and on the distal end side relative to an observation means forming surface 72 as described below, the distance between the ultrasonic transducer 50 and the opening 58 can be reduced. Accordingly, it is possible to reduce the distance from a position of a treatment tool that has just been led out from the opening 58 to a treatment target position to be treated with the treatment tool. As a result, horizontal displacement of the treatment tool can be reduced, and the treatment tool can be inserted to a target position.

As illustrated in FIG. 3, the standing wall portion 68 is formed around the opening 58. By forming the standing wall portion 68, horizontal displacement of a treatment tool that is led out from the opening 58 can be prevented, and treatment of a target position can be stably performed by using the treatment tool. It is sufficient that the standing wall portion 68 can prevent horizontal displacement of a treatment tool, and it is not necessary that the standing wall portion 68 be formed around the entirety of the opening 58. To be specific, preferably, the standing wall portion 68 is formed so as to stand upward from both sides of the direction in which the treatment tool is led out from the opening 58. In the first embodiment, the standing wall portion 68 stands from the entirety of the opening forming surface 70 diagonally upward in the direction of the opening 58. The opening forming surface 70 and the standing wall portion 68 may be integrally formed.

Regarding the standing wall portion 68, in the example illustrated in FIG. 2, the standing wall portion 68 is disposed at both end portions of the opening 58 in the direction of the axis 38 of the distal end portion body 36. However, the standing wall portion 68 may be disposed only on the proximal end side of the opening 58. By disposing the standing wall portion 68 only on the proximal end side, a body cavity wall (tissue) can be made to closely contact even the proximal end side of the ultrasound transmitting/receiving surface 52 of the ultrasonic transducer 50. By making the body cavity wall closely contact the ultrasound transmitting/receiving surface 52, the distance between the opening 58 and the body cavity wall can be reduced. Therefore, the position of a treatment tool led out from the opening 58 can be prevented from becoming displaced by a large distance, and treatment can be performed at a target position.

The distal end portion body 36 has light-guiding recessed wall portions 76L and 76R, where left-side and right-side portions of an opening forming surface portion 74 of the opening forming surface 70 are cut off diagonally downward. By forming the light-guiding recessed wall portions 76L and 76R in this way, blocking of illumination light from the illumination windows 46L and 46R is suppressed, and occurrence of nonuniform illumination and generation of a shadowed region can be prevented. The light-guiding recessed wall portions 76L and 76R need not be cut off diagonally downward, and may be cut off in the vertical direction or may be cut off diagonally forward.

The observation window 44 is disposed in the observation means forming surface 72 located on the proximal end side of the opening forming surface 70. Inside of the observation window 44, an imaging system unit, in which an image-forming optical system and a solid-state imaging element of an imaging unit are integrally assembled, is disposed. Thus, when light from a treatment target portion that is in the field of view of the imaging unit enters through the observation window 44, the light is focused via the image-forming optical system as an observation image on the solid-state imaging element. That is, an image of the treatment target portion is captured by the solid-state imaging element.

The observation means forming surface 72, in which the observation window 44 is disposed, is formed of a surface that has a normal component toward the distal end side in the direction of the axis 38 of the distal end portion body 36. In the first embodiment, the observation means forming surface 72 is formed as an inclined surface that is inclined upward toward the proximal end side of the distal end portion 34. By forming the observation means forming surface 72 as a surface having a normal component toward the distal end side and by forming the observation window 44 in the observation means forming surface 72, the position from which a treatment tool is led out from the opening 58 can be placed within the field of view of the observation window 44. Accordingly, a treatment tool can be checked through the observation window 44 from the opening 58 to a treatment target position. The observation means forming surface 72 may be formed of a perpendicular surface that is perpendicular to the direction of the axis 38 of the distal end portion body 36.

The illumination windows 46L and 46R are formed in the observation means forming surface 72 on both sides of the observation window 44. A light emitting portion of the illumination portion is disposed inside of the illumination windows 46L and 46R. From the light emitting portion, illumination light that is transmitted from the light source device, which is connected to the universal cord 14, through the light guide is emitted. The illumination light illuminates a treatment target position in the field of view of the image-capturing portion through the illumination windows 46L and 46R.

The air/water supply nozzle 48 is formed at the observation means forming surface 72. When the air/water supply button 20 illustrated in FIG. 1 is operated, the air/water supply nozzle 48 illustrated in FIG. 2 ejects a cleaning liquid, water, air, or the like (hereinafter, referred to as "cleaning liquid or the like") toward the observation window 44 to perform cleaning or the like of the observation window 44.

The observation means forming surface 72 has a deflecting portion 78 at a position that is opposite the air/water supply nozzle 48 with the observation window 44 therebetween. The deflecting portion 78 is disposed so as to protrude from the observation means forming surface 72. The deflecting portion 78 may be integrally formed with the observation means forming surface 72 or may be fixed as an independent portion. A cleaning liquid or the like that is ejected from the air/water supply nozzle 48 toward the observation window 44 collides with the deflecting portion 78. The cleaning liquid or the like that has collided with the deflecting portion 78 is deflected toward the opening 58, and is supplied to the opening 58. Thus, cleaning or the like of the inside of the opening 58 is performed.

The shape of the deflecting portion 78 is not particularly limited, as long as the deflecting portion 78 can deflect the cleaning liquid or the like that has passed the observation window 44 toward the opening 58. For example, as illustrated in FIG. 2, the deflecting portion 78 may be formed of two surfaces 78A and 78B, which are flat surfaces that are perpendicular to each other. The deflecting portion 78 may be formed of a surface that has a curved shape, such as an arc shape, an elliptical arc shape, or a parabolic shape.

As illustrated in FIGS. 4 and 5, in the present embodiment, the distal end portion body 36 includes a cleaning communication hole 84, through which the erecting base housing portion 62 communicates with the outside, in a wall surface opposite a side where the opening 58 of the erecting base housing portion 62 is disposed. By forming the cleaning communication hole 84, it is possible to insert a cleaning tool, such as a brush or a syringe, into the erecting base housing portion 62 from the cleaning communication hole 84, and therefore cleaning of the back side of the erecting base 60 and the surrounding part can be easily performed.

Figure 7:
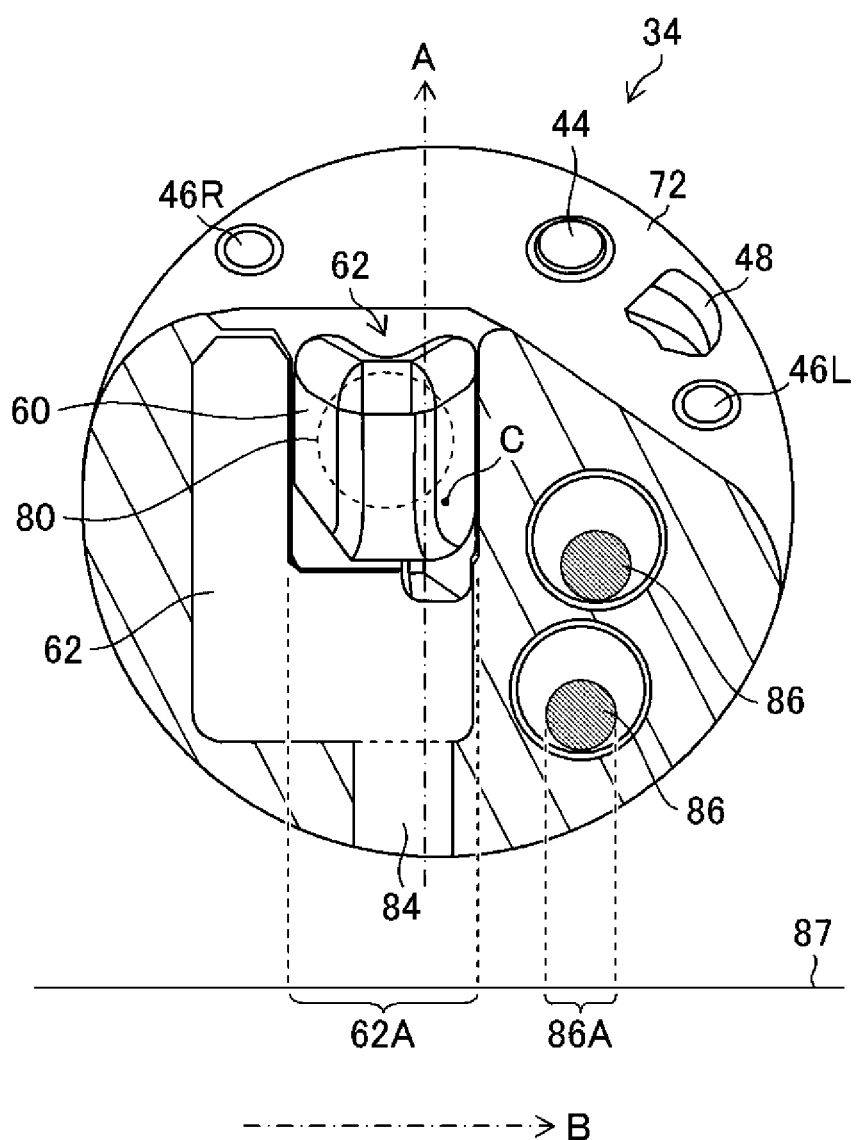
FIG. 7 is a sectional view taken along line 7-7 of FIG. 3.

FIG. 7 is a sectional view of the distal end portion body 36, taken along line 7-7 in FIG. 3. Signal cables 86 are disposed in the distal end portion body 36. The signal cables 86 are cables that connect the ultrasonic vibrators (not shown) of the ultrasonic transducer 50 illustrated in FIG. 2 to system components. The signal cables 86 are disposed in the insertion section 12 and the universal cord 14 in FIG. 1. As illustrated in FIG. 7, when the signal cable 86 and the erecting base housing portion 62 are projected onto a plane 87 that is perpendicular to the first direction indicated by arrow A, the signal cable 86 is disposed in a region 86A that is different from a region 62A where the erecting base housing portion 62 is disposed. That is, as illustrated in FIG. 7, the signal cable 86 is disposed on one side of the erecting base housing portion 62 in the second direction (on the right side of the erecting base housing portion 62 in FIG. 7). At this time, the erecting base housing portion 62 is disposed offset from the center position C of the distal end portion body 36 toward the other side in the second direction (the left side of the center position C in FIG. 7).

By disposing the erecting base housing portion 62 to be offset from the center position C of the distal end portion body 36 toward the other side in the second direction, the erecting base housing portion 62 and the signal cables 86 can be arranged in the second direction.

Figure 8:
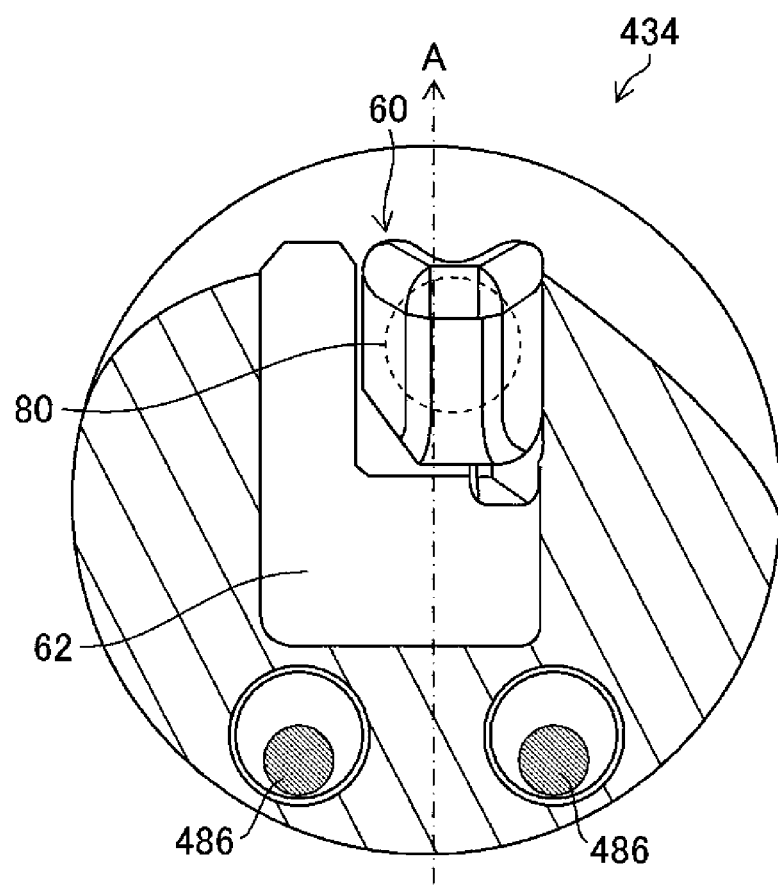
FIG. 8 is a sectional view of a distal end portion of an endoscope (comparative example)

In contrast, FIG. 8 is a sectional view of a distal end portion 434 of an ultrasonic endoscope according to another example as a comparative example. In the distal end portion 434 illustrated in FIG. 8, signal cables 486 are disposed on the other side of the erecting base housing portion 62 in the first direction (below the erecting base housing portion 62 in FIG. 8). Instead of disposing the signal cables 486 on the other side of the erecting base housing portion 62 in the first direction, by disposing the signal cables 86 in the second direction of the erecting base housing portion 62 as illustrated in FIG. 7, the cleaning communication hole 84 can be formed on the other side of the erecting base housing portion 62 in the first direction (below the erecting base housing portion 62 in FIG. 5). Moreover, the erecting base housing portion 62 can be disposed in a lower part of the distal end portion body 36. By disposing the erecting base housing portion 62 in the lower part, the distance from the cleaning communication hole 84 to the erecting base 60 can be reduced, and cleaning of the back side of the erecting base 60 and the surrounding part can be easily performed.

In FIG. 7, two signal cables 86 are illustrated. However, the number of signal cables 86 is not particularly limited, and may be two, one, three, or more. The shape of the signal cable 86 is not particularly limited, and a flexible circuit board or a signal cable having an elliptical or rectangular shape may be used.

As illustrated in FIG. 5, preferably, the distal end portion body 36 has a cover 88 that is attachable to and removable from the cleaning communication hole 84. When inserting the insertion section 12 into the body cavity of a subject, by attaching the cover 88 to the cleaning communication hole 84 and closing the cleaning communication hole 84, adhesion of contaminants to the erecting base housing portion 62 can be suppressed. When cleaning the erecting base 60, by removing the cover 88 from the cleaning communication hole 84, cleaning of the back side of the erecting base and the surrounding part can be performed by using a cleaning tool.

As illustrated in FIG. 7, by disposing the erecting base housing portion 62 in a lower part of the distal end portion body 36, the positional relationship among the components of the distal end portion body 36 can be made as follows. The positional relationship among the opening 58, an upper edge 68a of the standing wall portion 68, the observation window 44, and the ultrasonic transducer 50 will be described.

As illustrated in FIG. 4, the position of the observation window 44 in the first direction (the up-down direction in FIG. 4) is located on a side opposite to the cleaning communication hole 84, when the position of the upper edge 68a of the standing wall portion 68 is defined as a reference position. That is, an axis 45 of the observation window 44, which extends from the center position of the observation window 44 parallel to the axis 38 of the distal end portion body 36, is located above the reference position. The reference position is the position of the upper edge 68a of the standing wall portion 68 when the standing wall portion 68 is provided as illustrated in FIG. 4, and is the position of the opening 58 when the standing wall portion 68 is not provided. When the standing wall portion 68 is provided, a treatment tool is led to the outside from the upper edge 68a or the front edge 68b of the standing wall portion 68. By locating the observation window 44 above the upper edge 68a of the standing wall portion 68 in this way, at a position where a treatment tool is led out from the opening 58, the treatment tool can be placed within the field of view of the observation window 44. Accordingly, the treatment tool can be guided to a target position, and the accuracy in positioning the treatment tool can be improved.

The upper edge 68a of the standing wall portion 68 is disposed so that H1≤H2 holds, where, in the first direction indicated by arrow A of the distal end portion body 36 in FIG. 4, H1 is the shortest distance from the cleaning communication hole 84 to the upper edge 68a of the standing wall portion 68, and H2 is the longest distance from the cleaning communication hole 84 to the outer peripheral surface of the ultrasound transmitting/receiving surface 52 of the ultrasonic transducer 50.

When the upper edge 68a is diagonally formed, the distance between the position of the lowest end of the upper edge 68a and the cleaning communication hole 84 is defined as H1. By disposing the upper edge 68a of the standing wall portion 68 and the ultrasonic transducer 50 so as to satisfy H1≤H2, when a treatment tool that has passed through the treatment tool insertion channel 82 is led out diagonally upward from the upper edge 68a or the front edge 68b of the standing wall portion 68, the treatment tool can be led out so as to be close to the ultrasonic transducer 50. Accordingly, the treatment tool can be reliably inserted to a position where ultrasonic observation is performed by using the ultrasonic transducer 50.

Preferably, the position of the uppermost part of the treatment tool lead-out port 80 is the same as the position of the uppermost part of the ultrasound transmitting/receiving surface 52 of the ultrasonic transducer 50 or below the position of the uppermost part of the ultrasound transmitting/receiving surface 52 of the ultrasonic transducer 50. A treatment tool passes through the treatment tool insertion channel 82 and is led out diagonally upward from the opening 58, which opens upward. Accordingly, by locating the treatment tool lead-out port 80 below the ultrasonic transducer 50, the treatment tool can be led out to the vicinity of the ultrasonic transducer 50.

As illustrated in FIG. 3, preferably, the observation window 44 is disposed offset from the erecting base housing portion 62 in the second direction indicated by arrow B. Here, the clause "the observation window 44 is disposed offset from the erecting base housing portion 62 in the second direction" means that, as illustrated in FIG. 3, in a top view, a center line 44A of the observation window 44 is displaced from a center line 60A of the erecting base 60 in the second direction indicated by arrow B. With such a structure, even in a state in which the erecting base 60 is erected and a treatment tool is led out from the opening 58, the field of view of the observation window 44 can be prevented from being blocked by the treatment tool and the erecting base 60, and a treatment target position can be reliably checked through the observation window 44.

Figure 9:
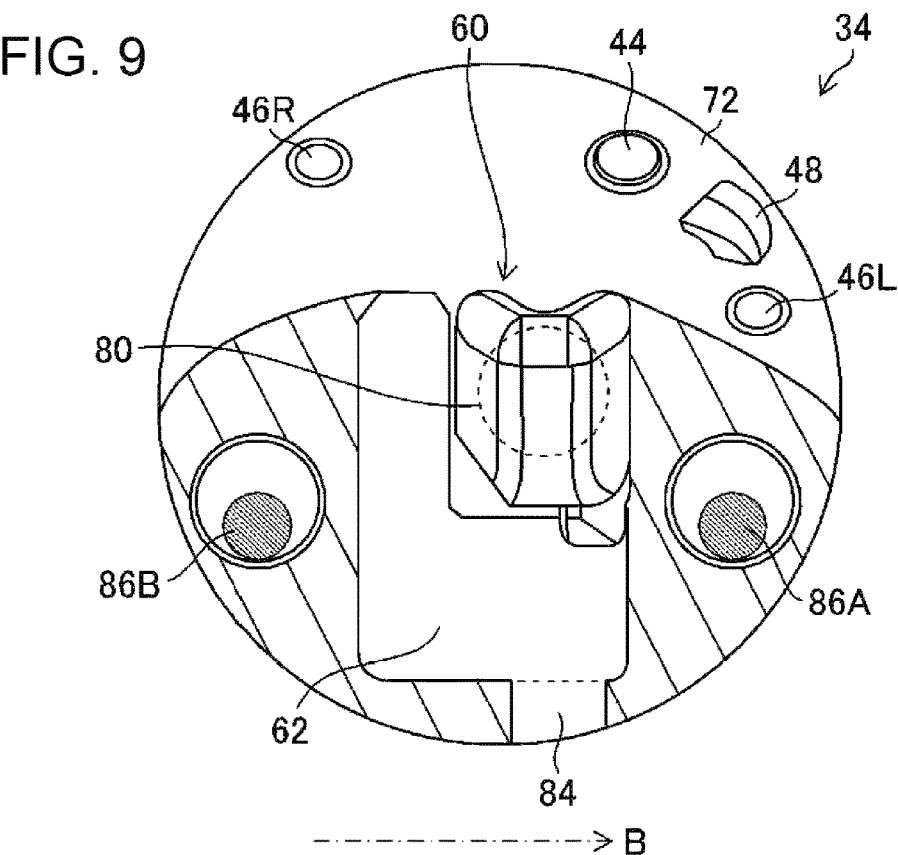
FIG. 9 is a sectional view of a distal end portion body, illustrating the disposition of signal cables according to a modification.

FIG. 9 is sectional view of the distal end portion body 36, illustrating another example of the disposition of the signal cables 86A and 86B in the distal end portion body 36. As illustrated in FIG. 9, among the two signal cables 86, the signal cable 86A (at least one of the signal cables) is disposed on one side in the second direction indicated by arrow B relative to the erecting base housing portion 62, and the signal cable 86B (at least another of the signal cables) is disposed on the other side in the second direction relative to the erecting base housing portion 62. By disposing the signal cables 86A and 86B in this way, the erecting base housing portion 62 can be lowered in the distal end portion body 36, the distance between the cleaning communication hole 84 and the erecting base 60 can be reduced, and cleaning of the back side of the erecting base 60 and the surrounding part can be easily performed. Although the external view of the sectional view shown in FIG. 9 is omitted, the positions of the observation window 44, the illumination windows 46L and 46R, and the air/water supply nozzle 48 may be appropriately set.

Second Embodiment

Figure 10:
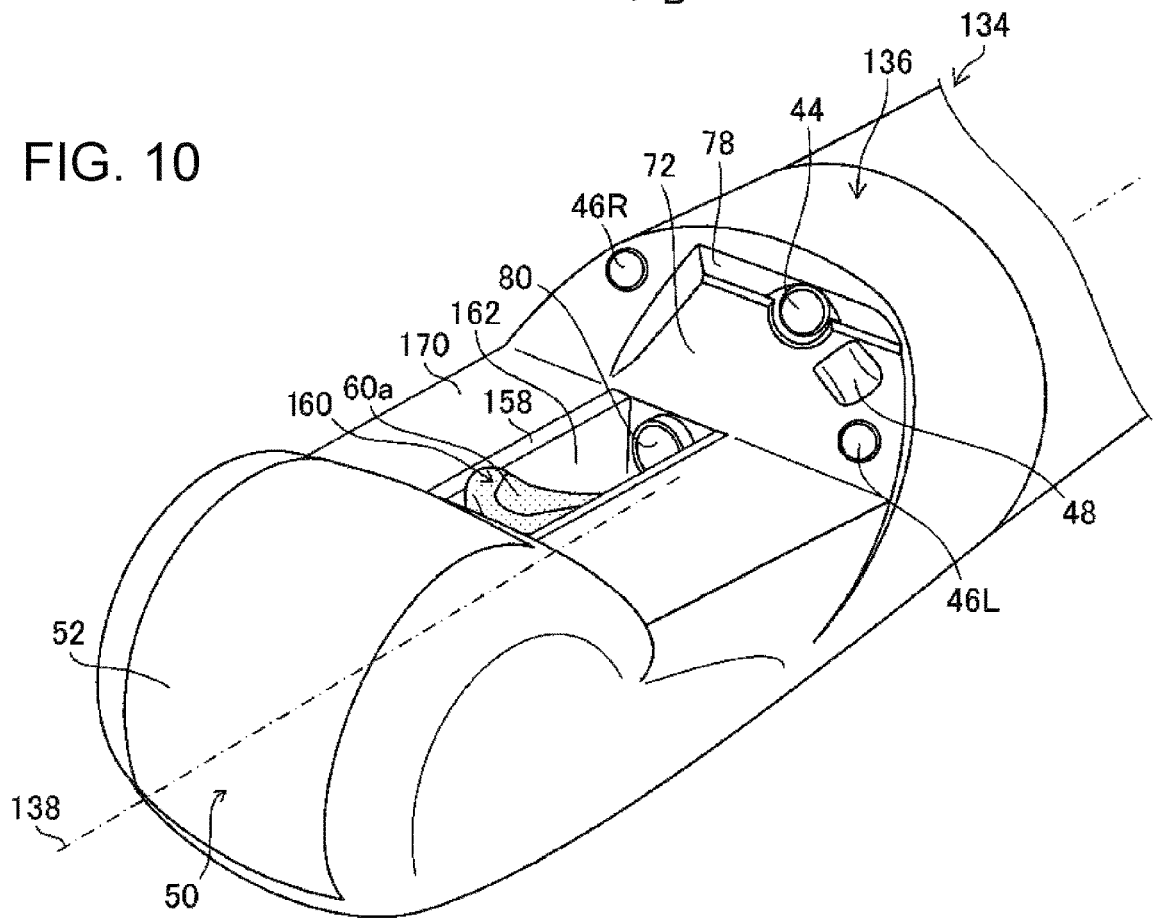
FIG. 10 is an external perspective view of a distal end portion of an insertion section according to a second embodiment.
Figure 11:
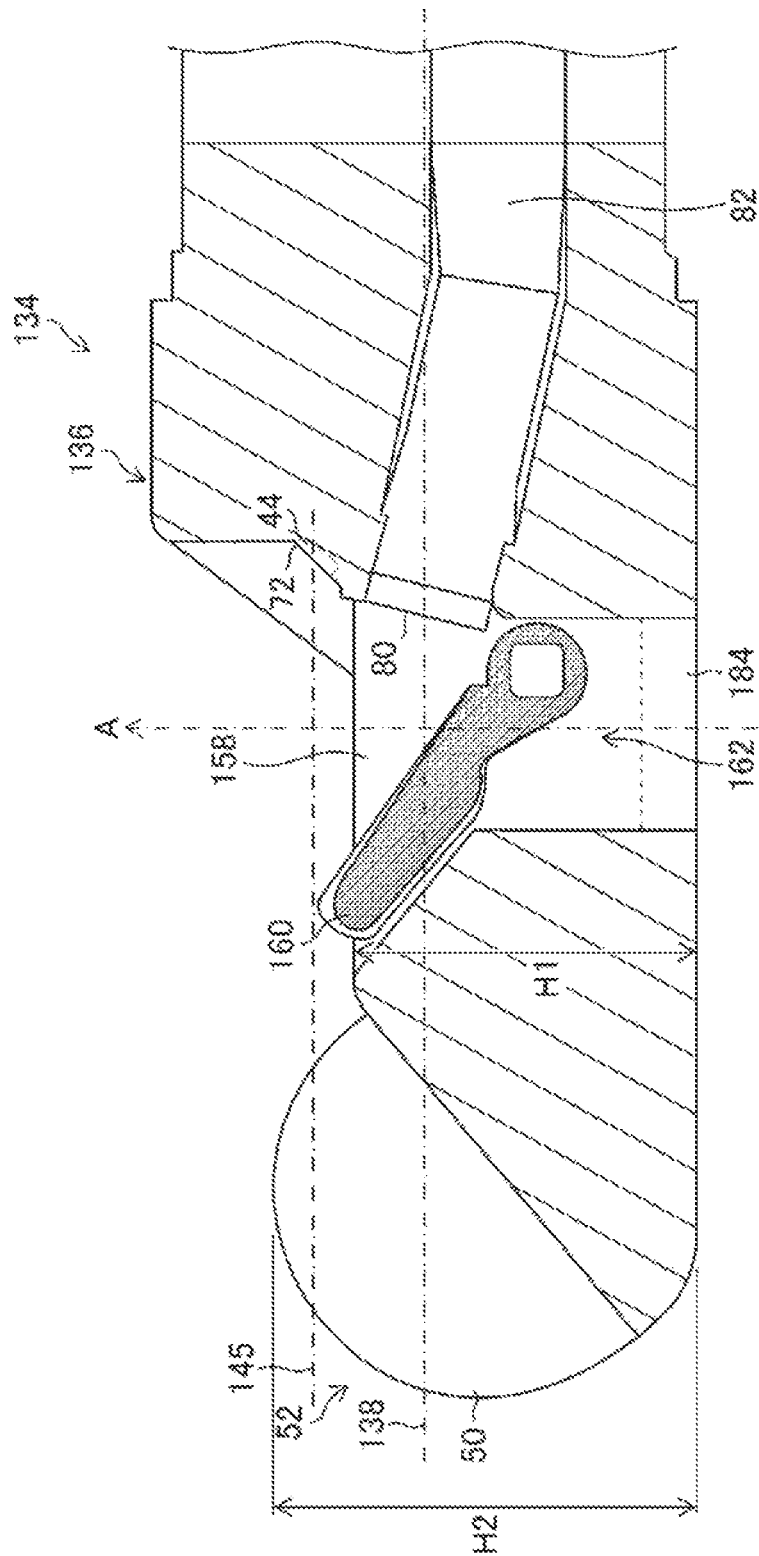
FIG. 11 is a side sectional view of the distal end portion of the insertion section according to the second embodiment.

FIG. 10 is an external perspective view of a distal end portion 134 according to a second embodiment, and FIG. 11 is a side sectional view. A distal end portion body 136 of the distal end portion 134 according to the second embodiment differs from the distal end portion body 36 according to the first embodiment illustrated in FIGS. 2 to 5 in that the distal end portion body 136 does not have a standing wall portion and a light-guiding recessed wall portion. In the description of the second embodiment illustrated in FIG. 10, members that are the same as those of the first embodiment illustrated in FIGS. 2 to 5 will be denoted by the same numerals and description of such members may be omitted.

Also with the distal end portion body 136 illustrated in FIGS. 10 and 11, by forming a cleaning communication hole 184 in a wall portion opposite to an opening 158 of an erecting base housing portion 162, the ease of cleaning the back surface of an erecting base 160 and the surrounding part can be improved.

As with the distal end portion body 136 according to the second embodiment, even without a standing wall portion, by setting the positional relationship between the opening 158, from which a treatment tool is led to the outside, and the observation window 44 so that the position of the opening 158 is located below an axis 145 of the observation window 44, the treatment tool led out from the opening 158 can be placed within the field of view of the observation window 44. The axis 145 is a line extending from the center position of the observation window 44 toward the distal end side, and is a line that is parallel to an axis 138 of the distal end portion body 136.

When a standing wall portion is not provided, in the first direction indicated by arrow A in FIG. 11, a position from which a treatment tool is led out from the distal end portion body 136 is the position of the opening 158, and, preferably, the positional relationship between the ultrasonic transducer 50 and the opening 158 satisfies the following expression. The opening 158 and the ultrasonic transducer 50 are disposed so that H1≤H2 holds, where H1 is the shortest distance from the cleaning communication hole 184 to the opening 158, and H2 is the longest distance from the cleaning communication hole 184 to the outer peripheral surface of the ultrasonic transducer 50. When an opening forming surface 170 illustrated in FIG. 10 is an inclined surface that is inclined downward toward the distal end side of the distal end portion body 136 and the opening 158 is diagonally formed, the distance to the position of the lowest end of the opening 158 is defined as H1. With such a structure, as with the first embodiment, a treatment tool can be led out so as to be close to the ultrasonic transducer 50.

Also in the second embodiment, by disposing the signal cables 86 in the second direction of the erecting base housing portion 162 as in the first embodiment illustrated in FIGS. 7 and 9, the erecting base housing portion 162 can be disposed in a lower part of the distal end portion body 136 in the first direction.

Third Embodiment

Figure 12:
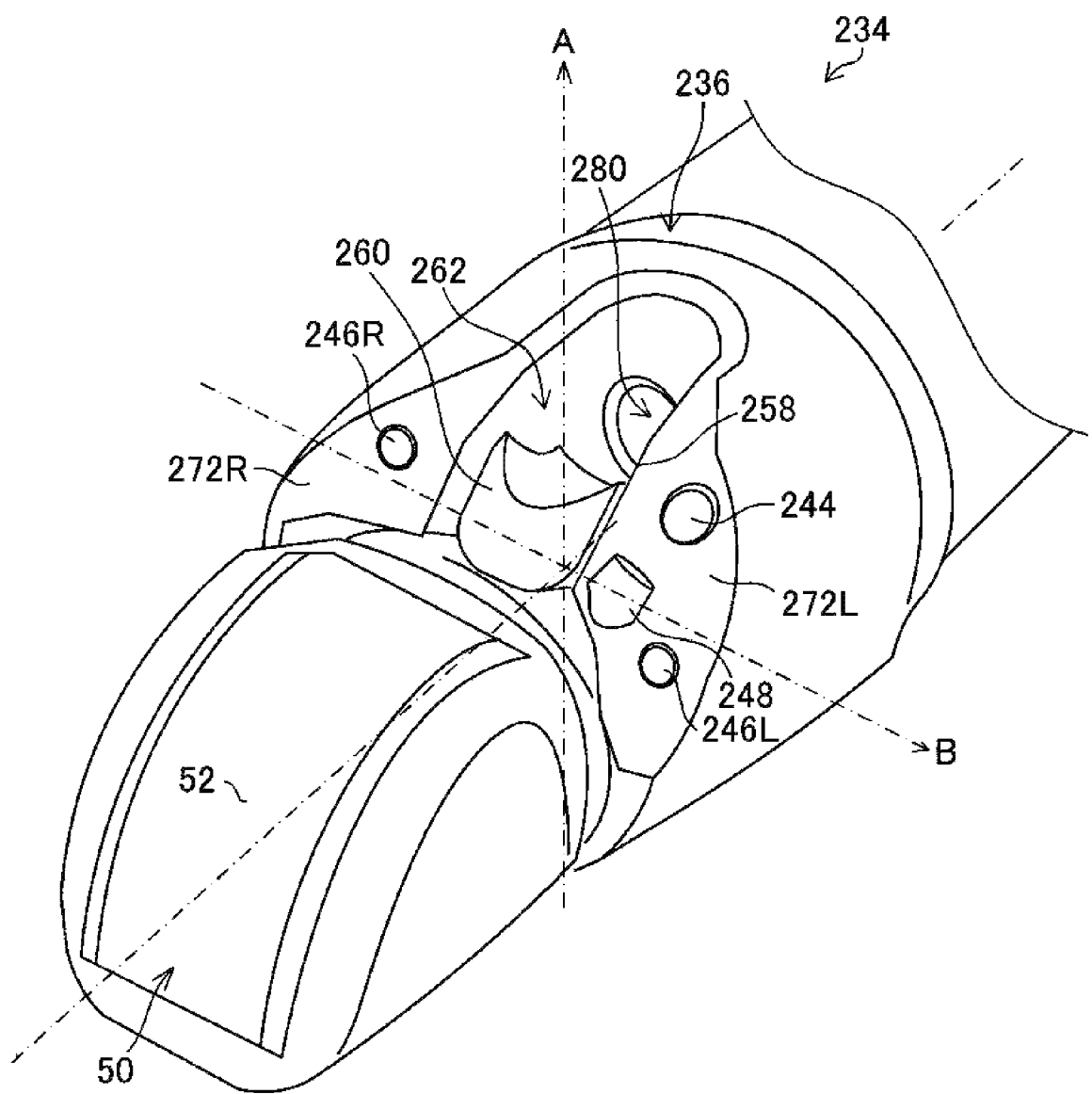
FIG. 12 is an external perspective view of a distal end portion of an insertion section according to a third embodiment.
Figure 13:
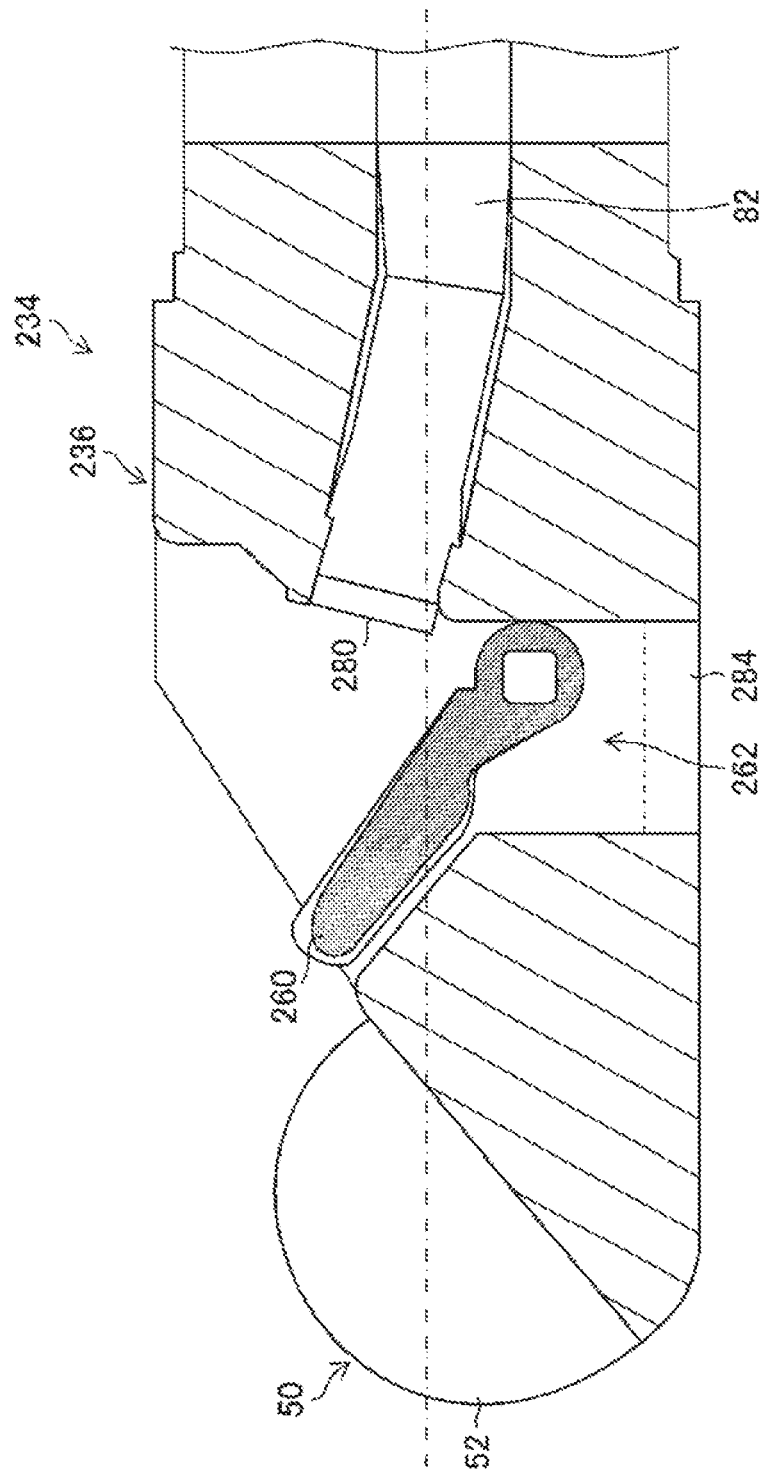
FIG. 13 is a side sectional view of the distal end portion of the insertion section according to the third embodiment.

FIG. 12 is an external perspective view of a distal end portion 234 according to the third embodiment, and FIG. 13 is a side sectional view. A distal end portion body 236 according to the third embodiment has, as a distal end surface of the distal end portion body 236, a left-side observation means forming surface 272L and a right-side observation means forming surface 272R that are disposed with a treatment tool lead-out port 280 interposed therebetween. The left-side observation means forming surface 272L has an observation window 244, an air/water supply nozzle 248, and an illumination window 246L. The right-side observation means forming surface 272R has an illumination window 246R. In the third embodiment, the left-side observation means forming surface 272L, in which the observation window 244 is disposed, is disposed on the distal end side relative to the treatment tool lead-out port 280 and is disposed in a second direction, indicated by arrow B, of an opening 258.

Also with the distal end portion body 236 according to the third embodiment, by forming a cleaning communication hole 284 in a wall portion opposite to the opening 258 of an erecting base housing portion 262, the ease of cleaning the back surface of an erecting base 260 and the surrounding part can be improved.

Also with the third embodiment, by disposing signal cables passing through the distal end portion 234 on a side of the erecting base housing portion 262, the erecting base housing portion 262 can be disposed in a lower part of the distal end portion body 236. Accordingly, the length of the cleaning communication hole 284 can be reduced and cleaning of the erecting base 260 can be easily performed.

In each of the first to third embodiments, a convex-type ultrasonic transducer has been described. However, the present invention is not limited to a convex-type ultrasonic transducer and can be applied also to a radial-type ultrasonic transducer.

REFERENCE SIGNS LIST 1 ultrasonic endoscope
10 operation unit
12 insertion section
14 universal cord
16 angle knob
18 erecting base operation lever
20 air/water supply button
22 suction button
24 treatment tool insertion opening
30 soft portion
32 bending portion
34, 134, 234, 434 distal end portion
36, 136, 236 distal end portion body
38, 138, axis of distal end portion body
40 base member
42 extension portion
44, 244 observation window
44A center line of observation window
45, 145 axis of observation window
46L, 46R, 246L, 246R illumination window
48, 248 air/water supply nozzle
50 ultrasonic transducer
52 ultrasound transmitting/receiving surface
58, 158, 258 opening
60, 61, 160, 260 erecting base
60A center line of erecting base
60a guide surface
62, 62A, 162, 262 erecting base housing portion
68 standing wall portion
68a upper edge
68b front edge
70, 170 opening forming surface
72 observation means forming surface
74 opening forming surface portion
76L, 76R light-guiding recessed wall portion
78 deflecting portion
80, 280 treatment tool lead-out port
82 treatment tool insertion channel
84, 184, 284 cleaning communication hole
86, 86A, 86B, 486 signal cable
87 plane
88 cover
272L left-side observation means forming surface
272R right-side observation means forming surface

What is claimed is:

1. An ultrasonic endoscope comprising:
   an ultrasonic transducer that has an ultrasonic vibrator;
   a distal end portion body that is disposed continuously with a proximal end side of the ultrasonic transducer;
   an erecting base housing portion that is disposed in the distal end portion body and that has an opening whose opening direction is one side in a first direction that is perpendicular to an axial direction of the distal end portion body or whose opening direction is a direction that has a component toward one side in the first direction and a component toward a distal end side in the axial direction of the distal end portion body;
   a treatment tool lead-out port that communicates with an inside of the erecting base housing portion and from which a treatment tool is led out;
   an erecting base that is disposed in the inside of the erecting base housing portion and that changes a lead out direction of the treatment tool led out from the treatment tool lead-out port; and
   a cleaning communication hole that is formed in a wall surface on a side opposite to a side where the opening of the erecting base housing portion is disposed and that communicates with an outside,
   wherein the ultrasonic endoscope has a signal cable that is connected to the ultrasonic vibrator,
   wherein, in a case where the signal cable and the erecting base housing portion are projected onto a plane that is perpendicular to the first direction, the signal cable is disposed in a region that is different from a region where the erecting base housing portion is disposed.

2. The ultrasonic endoscope according to claim 1, comprising:
   an observation window that is disposed in the distal end portion body and through which a subject is observed,
   wherein a position of the observation window in the axial direction of the distal end portion body is located on a proximal end side relative to the erecting base housing portion.

3. The ultrasonic endoscope according to claim 2,
   wherein a position of the observation window in the first direction is located on a side opposite to the cleaning communication hole when a position of the opening is defined as a reference position.

4. The ultrasonic endoscope according to claim 2,
   wherein the observation window is disposed offset from the erecting base housing portion in a second direction that is perpendicular to the first direction.

5. The ultrasonic endoscope according to claim 1, comprising:
   an observation window that is disposed in the distal end portion body and through which a subject is observed,
   wherein a position of the observation window in the axial direction of the distal end portion body is located on a distal end side relative to the erecting base housing portion.

6. The ultrasonic endoscope according to claim 5,
   wherein a position of the observation window in the first direction is located on a side opposite to the cleaning communication hole when a position of the opening is defined as a reference position.

7. The ultrasonic endoscope according to claim 5,
   wherein the observation window is disposed offset from the erecting base housing portion in a second direction that is perpendicular to the first direction.

8. The ultrasonic endoscope according to claim 1,
   wherein, when viewed in the axial direction of the distal end portion body, the erecting base housing portion is disposed offset from a center position of the distal end portion body in a second direction that is perpendicular to the first direction, and
   wherein the signal cable is disposed in the second direction of the erecting base housing portion.

9. The ultrasonic endoscope according to claim 8,
   wherein, when viewed in the axial direction of the distal end portion body, among a plurality of the signal cables that are connected to the ultrasonic vibrator, at least one of the plurality of the signal cables is disposed on a first side in a second direction of the erecting base housing portion, and at least another of the plurality of the signal cables is disposed on a second side in the second direction of the erecting base housing portion.

10. The ultrasonic endoscope according to claim 8,
    wherein, when viewed in the axial direction of the distal end portion body, a plurality of the signal cables that are connected to the ultrasonic vibrator are disposed on a side of the erecting base housing portion in a second direction where an observation window is disposed.

11. The ultrasonic endoscope according to claim 1,
    wherein, when viewed in the axial direction of the distal end portion body, among a plurality of the signal cables that are connected to the ultrasonic vibrator, at least one of the plurality of the signal cables is disposed on a first side in a second direction of the erecting base housing portion, and at least another of the plurality of the signal cables is disposed on a second side in the second direction of the erecting base housing portion.

12. The ultrasonic endoscope according to claim 1,
    wherein, when viewed in the axial direction of the distal end portion body, a plurality of the signal cables that are connected to the ultrasonic vibrator are disposed on a side of the erecting base housing portion in a second direction where an observation window is disposed.

13. The ultrasonic endoscope according to claim 1,
    wherein the distal end portion body comprises a cover that is removably attached to the cleaning communication hole.

14. The ultrasonic endoscope according to claim 1,
    wherein an expression H1≤H2 holds, where, in the first direction of the distal end portion body, H1 is a shortest distance from the cleaning communication hole to the opening, and H2 is a longest distance from the cleaning communication hole to an outer peripheral surface of the ultrasonic transducer.

15. The ultrasonic endoscope according to claim 1,
    wherein the ultrasonic transducer has an ultrasound transmitting/receiving surface that is formed in a curved shape in the axial direction of the distal end portion body.

16. The ultrasonic endoscope according to claim 1,
    wherein a distal end part of the erecting base protrudes from the erecting base housing portion, in a state where the erecting base is in a prostrate position.

17. The ultrasonic endoscope according to claim 1,
    wherein an upper region of the wall surface on the distal end side of the erecting base housing portion is formed inclined downward toward the proximal end side.

18. The ultrasonic endoscope according to claim 1,
    wherein the erecting base includes a portion through which a rotation shaft extends therethrough, the rotation shaft configured to rotate the erecting base, wherein in a case where the cleaning communication hole is viewed from the outside to the first direction, a region of a proximal end side of the erecting base, including the portion of the erecting base having the rotation shaft extending therethrough, is disposed at a position overlapping with the cleaning communication hole.

19. The ultrasonic endoscope according to claim 1, wherein the cleaning communication hole includes at least two inner standing wall surfaces of the cleaning communication hole that intersect with the axial direction, and of the at least two inner standing wall surfaces of the cleaning communication hole, the inner standing wall surface of the cleaning communication hole on a proximal end side of the cleaning communication hole and a region on an other side of a treatment instrument outlet in the first direction are on a same plane.

20. The ultrasonic endoscope according to claim 19, wherein a length of one of the at least two inner standing wall surfaces of the cleaning communication hole in a second direction is shorter than a length of the erecting base housing portion in the second direction where the treatment instrument outlet is disposed.

* * * * *